United States Patent
Tanzer et al.

(10) Patent No.: US 7,675,219 B2
(45) Date of Patent: Mar. 9, 2010

(54) METHOD FOR CONTROLLING AN ULTRASONIC UNIT OF AN ULTRASONIC CLEANING SYSTEM

(75) Inventors: Armin Tanzer, Gravenwiesbach (DE); Bernhard Jung, Ober-Morlen (DE)

(73) Assignee: Medtronic GmbH, Usingen (DE)

( * ) Notice: Subject to any disclaimer, the term of this patent is extended or adjusted under 35 U.S.C. 154(b) by 321 days.

(21) Appl. No.: 11/730,775

(22) Filed: Apr. 4, 2007

(65) Prior Publication Data

US 2007/0236103 A1    Oct. 11, 2007

(30) Foreign Application Priority Data

Apr. 5, 2006   (DE) .................. 10 2006 016 359

(51) Int. Cl.
*H01L 41/09* (2006.01)
*A61C 1/07* (2006.01)
*A61C 1/00* (2006.01)

(52) U.S. Cl. .................. 310/317; 310/323.18; 433/86; 433/101; 433/118; 433/119; 601/2; 601/22

(58) Field of Classification Search .................. 310/317, 310/323.18; 433/86, 101, 118, 119; 601/2, 601/22

See application file for complete search history.

(56) References Cited

U.S. PATENT DOCUMENTS

| | | | | | |
|---|---|---|---|---|---|
| 4,371,816 | A | * | 2/1983 | Wieser | 318/118 |
| 5,578,888 | A | * | 11/1996 | Safabakhsh | 310/328 |
| 6,545,390 | B1 | * | 4/2003 | Hahn et al. | 310/317 |
| 2004/0063064 | A1 | * | 4/2004 | Feine | 433/119 |
| 2009/0047624 | A1 | * | 2/2009 | Tsai | 433/119 |

FOREIGN PATENT DOCUMENTS

DE    32 15 748 A1    11/1983
DE    697 29 738 T2    8/2005

* cited by examiner

*Primary Examiner*—Thomas M Dougherty
(74) *Attorney, Agent, or Firm*—Hoffman, Wasson & Gitler

(57) ABSTRACT

The invention relates to a method for controlling an ultrasonic unit f an ultrasonic cleaning system with at least one control unit, one generator unit and one hand-held unit containing the ultrasonic unit and one switching module provided for starting the ultrasonic unit, wherein mechanical oscillations can be generated via the ultrasonic unit and transmitted to an instrument that is mechanically connected to the ultrasonic unit. In a preferred embodiment, the resonant frequency required for operation of the ultrasonic unit in resonance is determined by a control routine executed in the control unit, and a control signal (ss) based on the determined resonant frequency is generated in the generator unit and is sent to the ultrasonic unit for operation of the ultrasonic unit in resonance.

15 Claims, 2 Drawing Sheets

METHOD FOR CONTROLLING AN ULTRASONIC UNIT OF AN ULTRASONIC CLEANING SYSTEM

BACKGROUND OF THE INVENTION

The invention relates to a method for controlling an ultrasonic unit of an ultrasonic cleaning system.

Ultrasonic cleaning systems for professional removal of tartar and/or plaque are sufficiently known in the art. These systems feature an instrument that is movably provided in a hand-held unit and that can be set in oscillation by means of an ultrasonic unit provided in the hand-held unit. There are two types of ultrasonic units: piezoelectric and magnetostrictive.

In piezoelectric ultrasonic units the oscillation is generated by the influence of AC voltage on a quartz crystal. Magnetostrictive ultrasonic units comprise an electromagnetic converter unit with a coil unit, by means of which an electric control signal generated in a control unit is converted into mechanical oscillation. For this purpose, a ferromagnetic core element is inserted into the electromagnetic converter unit and the coil unit is energized by the electric control signal.

The electric control signal is an AC signal that produces a magnetic alternating field in the coil unit. The magnetic alternating field creates a periodic length change of the ferromagnetic core element in the form of a mechanical oscillation ("ultrasonic sound"). For transferring the mechanical oscillations to the instrument, the ferromagnetic core element is connected with the instrument by means of mechanical coupling.

Based on the dimensions of the electromagnetic converter unit and of the coil unit, a resonant frequency is generated for the respective electromagnetic converter unit, resulting in periodic oscillations with a maximum amplitude in the ferromagnetic core element. The periodic oscillations occur in the case of resonance as a stationary wave and are transmitted to the instrument connected to the ultrasonic unit, for example a working tip. To ensure that the electromagnetic converter unit achieves the maximum possible power output, it is necessary to operate it in resonance. The resonant frequency of the converter unit is dependent on numerous marginal conditions that frequently change during operation of the ultrasonic cleaning system and necessitate retuning of the resonant frequency.

It is an object of the present invention is to present a method for controlling an ultrasonic unit of an ultrasonic cleaning system, which with maximum power output enables easy operation and patient-friendly functioning of the ultrasonic cleaning system.

SUMMARY OF THE INVENTION

This object is achieved by the method wherein mechanical oscillations are generated via an ultrasonic unit and transmitted to an instrument that is mechanically connected to the ultrasonic unit.

An essential aspect of the method according to the invention is the fact that after actuating the switching module by a control routine executed in the control unit, the resonant frequency required for operation of the ultrasonic unit in resonance is determined and a control signal based on the determined resonant frequency is generated in the generator unit and is sent to the ultrasonic unit for operation of the ultrasonic unit in resonance. A particular advantage is that the resonant frequency is set very quickly, so that it can be executed again immediately after actuation of the switching module by the user of the system. Since the resonant frequency is constantly updated, this significantly improves the functioning of the system, enabling patient-friendly removal of tartar or plaque, for example, from the tooth surface.

BRIEF DESCRIPTION OF THE DRAWINGS

In the following, the method according to the invention is described in more detail based on one exemplary embodiment with reference to the drawings, wherein.

DETAILED DESCRIPTION OF THE INVENTION

Figure 1:
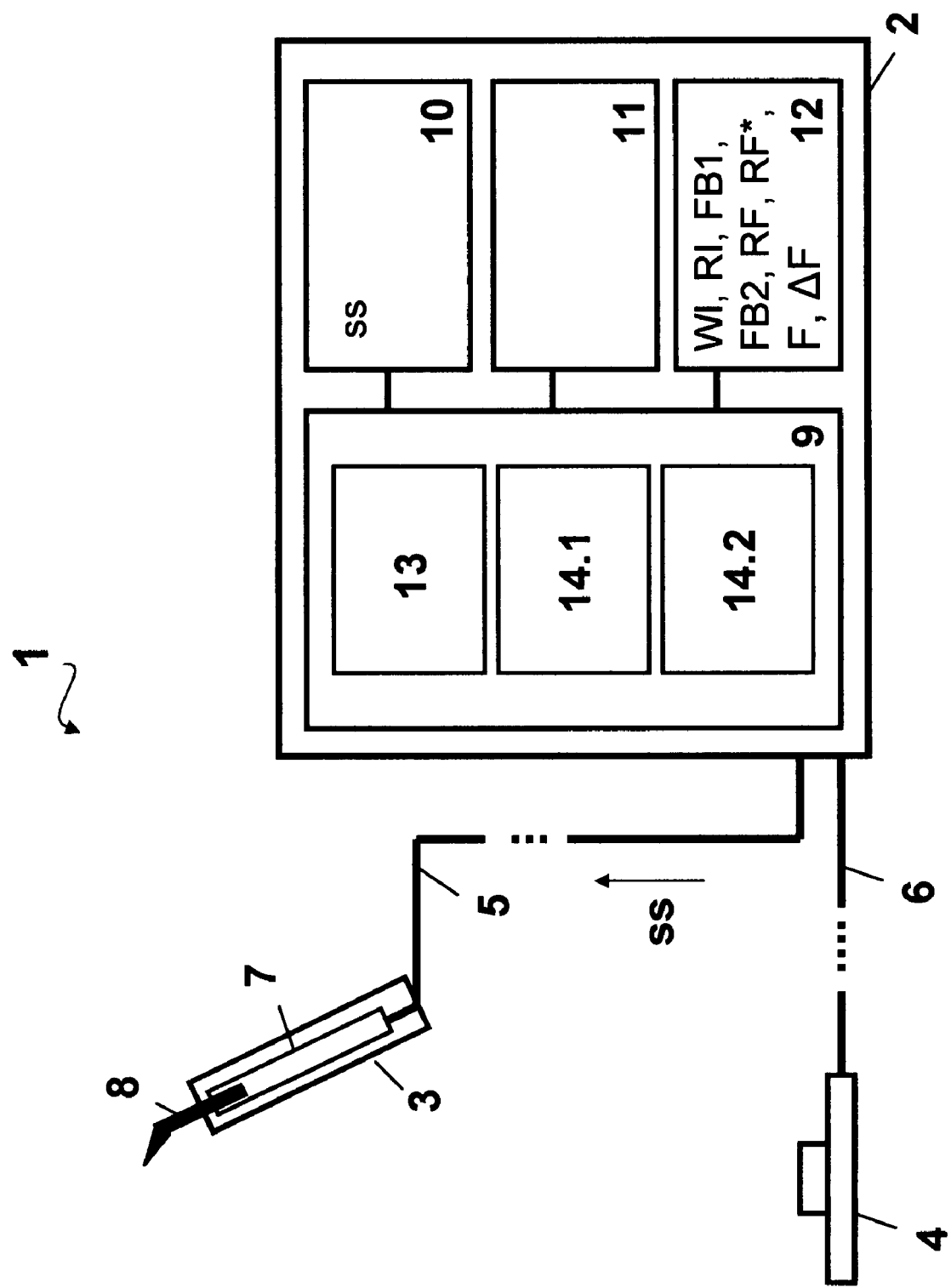
FIG. 1 shows an exemplary embodiment in a block diagram of an ultrasonic cleaning system and FIG. 2 shows an exemplary embodiment in a sequence diagram of the method according to the invention for controlling the ultrasonic unit of an ultrasonic cleaning system depicted in FIG. 1.

In FIG. 1, an ultrasonic cleaning system 1 is depicted in a block diagram as an exemplary embodiment that is preferably used for removing tartar and/or plaque for dental hygiene.

The ultrasonic cleaning system 1 contains of a control device 2, a hand-held unit 3 and a switching module 4; the hand-held unit 3 is connected to the control unit 2 via first connecting lines 5 and the switching module 4 is connected to the control unit via second connecting lines 6. In a preferred embodiment, the switching module 4 is designed as a foot switching module separate from the control device 2 and the hand-held unit 3 or it is integrated in the hand-held unit 3. The switching module 4 connected with the control device by means of second connecting lines 6 is provided for controlling the control device 2, in particular for switching on or switching off an ultrasonic unit 7 contained in the hand-held unit 3.

The ultrasonic unit 7 is connected, for example by mechanical connecting means (not depicted in FIG. 1), to an instrument 8, for example a working tip or chisel. Different instruments 8 featuring different working surfaces are provided for the various dental hygiene applications and can be modularly connected with the respective hand-held unit 3 or with a tool holder of its ultrasonic unit 7. In addition, hand-held units 3 equipped with ultrasonic units 7 of different power outputs can be provided with tool holders for the modular instruments 8, which can be exchanged easily and quickly by the user of the ultrasonic cleaning system 1. The hand-held units 3 can have different resonant frequencies depending on the ultrasonic unit 7 used.

For generating a mechanical oscillation, the ultrasonic unit 7 features an electromagnetic converter unit (not depicted in FIG. 1), which is supplied with at least one control signal ss with a pre-defined frequency F, preferably an AC signal, for generation of a magnetic alternating field via the first connecting lines 5. Based especially on the frequency F of the supplied control signal ss, the instrument 8 provided movably in the hand-held unit 3 is set in oscillation mechanically, so that the instrument 8 or its working surface executes scraping or slight hammering movements. These movements cause a mechanical reciprocation between the oscillating working surface and the tooth surface to be treated, so that tartar or plaque on the tooth surface can be removed incrementally.

Furthermore, the control device 2 features a control unit 9, to which a generator unit 10, a measuring unit 11 and a storage unit 12 are connected. For controlling the instrument 8, the control unit 9 features a control routine 13. The control routine 13 features a coarse tuning routine 14.1 for coarse tuning of the resonant frequency RF required for operation of the ultrasonic unit 7 and a fine tuning routine 14.2 for fine tuning, both of which are started for example by the control routine 13 and executed in the control unit 9. The parameters determined by the control routine 13 and/or the coarse and/or fine tuning routine 14.1, 14.2 or parameters required for their execution are stored in the storage unit 12 connected to the control unit 9 and loaded from said storage unit.

Figure 2:
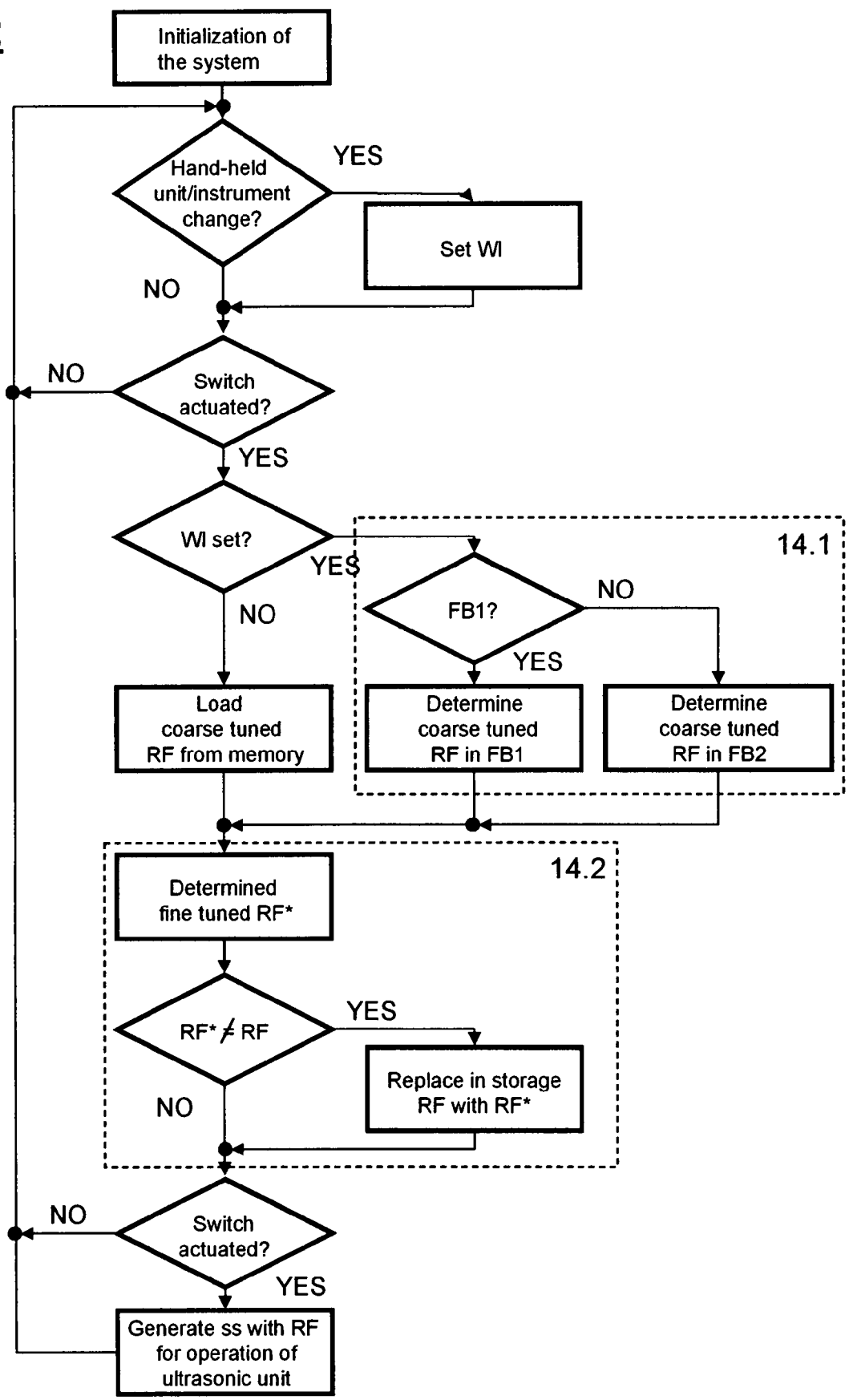

In FIG. 2 the method according to the invention is in an exemplary embodiment based on a sequence diagram, which preferably is implemented via programming means by the control routine 13 and the coarse and/or fine tuning routine 14.1, 14.2.

After initialization of the ultrasonic cleaning system 1, the control routine 13 determines whether the hand-held unit 3 and/or the instrument 8 located within the hand-held unit 3 has been exchanged. If the hand-held unit 3 and/or the instrument 8 located in the hand-held unit 3 have been exchanged, then the corresponding exchange information WI is generated by the control routine 13 and stored in the connected storage unit 12. In a preferred embodiment the exchange information WI takes the form of a flag, which is set in the event of an exchange of the hand-held unit 3 and/or the instrument 8.

After storing of the exchange information WI or in the event that the hand-held unit 3 has not been replaced, it is determined in a further step whether the switching module 4 has been actuated. If the switching module 4 has not been actuated, the procedure described above begins anew, immediately after initialization of the system, i.e. the control routine 13 is automatically reset to the state after initialization. If on the other hand the switching module 4 has been actuated, then the control routine 13 determines whether exchange information WI is stored in the ultrasonic cleaning system 1 or in the storage unit 12.

If exchange information WI is present, i.e. if a flag has been set, the coarse tuning routine 14.1 for determining a coarse tuned resonant frequency RF is started. The coarse tuning routine 14.1 analyzes, for example, the value of the existing exchange information WI or resonance information RI stored in the ultrasonic unit 7, for example a jumper module, and based on this information the frequency range FB1, FB2 to be searched for determining the coarse tuned resonant frequency RF is determined. Due to the value of the exchange information WI or the stored resonant information RI, at least one first or one second frequency range FB1, FB2 is specified, which is to be analyzed or searched for determining the coarse tuned resonant frequency RF. The first or second frequency range FB1, FB2 is for example likewise stored in the storage unit 12, and the range limits of the first or second frequency range FB1, FB2 can be configured individually. In a preferred embodiment, the first frequency range FB1 to be analyzed encompasses the range from ca. 17 to 19 kHz and the second frequency range FB2 encompasses the ranges from ca. 23.5 to 26.5 kHz and 28 to 32 kHz.

For the analysis of the first frequency range FB1, a control signal ss with a frequency F is generated by the generator unit 10, controlled by the control routine 13, which (signal) is sent to the ultrasonic unit 7 and by means of which a mechanical oscillation of the ultrasonic unit 7 is produced. During this process, the frequency F is increased incrementally from the lowest frequency of the first frequency range FB1 to the highest frequency of the first frequency range FB1. Alternatively, the frequency F can be decreased incrementally from the highest frequency of the first frequency range FB1 to the lowest frequency of the first frequency range FB1. For the respectively configured frequency F, the corresponding current amplitude for example is determined by the measuring unit 11, and the maximum current flowing through the coil element of the electromagnetic converter element is measured by the coarse tuning routine 14.1. The coarse tuned resonant frequency RF is the frequency at which the measured current amplitude accepts its maximum, i.e. at which the ultrasonic unit 7 is at maximum capacity. The coarse tuned resonant frequency RF is then stored for example in the storage unit 12.

If a second frequency range FB2 is specified by the value of the exchange information WI or the resonance information RI, then at least one second frequency range FB2 is searched or analyzed analogously to the first frequency range FB1 in order to determine the coarse tuned resonant frequency RF.

If no exchange information WI exists, then the last stored coarse tuned resonant frequency RF is loaded from the storage unit 12; otherwise, the previously determined and stored coarse tuned resonant frequency RF is used for the subsequent steps. Before operation of the ultrasonic unit 7 with the determined coarse tuned resonant frequency RF, the fine tuning routine 14.2 is started via the control routine 13 and fine tuning of the coarse tuned resonant frequency RF takes place. For this purpose, a fine tuned resonant frequency RF* is determined by the fine tuning routine 14.2 executed in the control unit 9, which (frequency) can deviate from the already determined coarse tuned resonant frequency RF, for example due to wear of the instrument 8, etc. occurring during operation of the ultrasonic cleaning system 1.

For fine tuning, a "wobble process" is used, in which the frequency F of the control signal ss, based on the coarse tuned resonant frequency RF, is increased slightly by a pre-defined tuning frequency $\Delta F$ and after each increase the current amplitude of the control signal ss having the resulting frequency RF+$\Delta F$ is determined. As long as the current amplitude increases, the frequency F continues to be increased incrementally by the pre-defined tuning frequency $\Delta F$. However, if the current amplitude decreases, then the fine tuned resonant frequency RF* is defined by the previous frequency RF+(n−1)*$\Delta F$.

Alternatively, the frequency F of the control signal ss, based on the coarse tuned resonant frequency RF, can be increased slightly by a pre-defined tuning frequency $\Delta F$ and the respective current amplitude of the control signal ss having the resulting frequency RF−$\Delta F$, RF−2*$\Delta F$, ..., RF−n*$\Delta F$ is determined. In a preferred embodiment the tuning frequency $\Delta F$ can be specified for individual users. For example, the tuning frequency can be $\Delta F$=0.1 kHz, so that based on a coarse tuned resonant frequency RF=18 kHz in a first run of the fine tuning routine 14.2 results in a frequency F of the control signal of, for example, 18.1 kHz or 17.9 kHz.

If the fine tuned resonant frequency RF* deviates from the coarse tuned resonant frequency RF, then the latter is replaced by the fine tuned resonant frequency RF* and is stored in the storage unit 12 as the resonant frequency RF allocated for operation of the hand-held unit 3 or the instrument 8 provided in the hand-held unit 3.

Afterwards, a control signal ss having the resonant frequency RF is generated in the generator unit 10 and is used for controlling the ultrasonic unit 7 of the ultrasonic cleaning system 1. Before controlling the ultrasonic unit 7 with the control signal ss generated in the generator unit 10 and therefore before operation of the ultrasonic unit 7 in resonance, it is determined in a preferred embodiment once again by means of a query whether the switching module 4 continues to be actuated or not.

This means that, independent of the execution of the coarse tuning routine 14.1, the fine tuning routine 14.2 fine tunes the coarse tuned resonance frequency RF in the control routine 13 before each operation of the ultrasonic unit 7.

The invention was described above based on one exemplary embodiment. It goes without saying that numerous modifications and variations are possible, without abandoning the underlying inventive idea upon which the invention is based.

REFERENCE LIST

1 ultrasonic cleaning system
2 control device
3 hand-held unit
4 switching module, for example foot switching module
5 first control lines
6 second control lines
7 ultrasonic unit
8 instrument
9 control unit
10 generator unit
11 measuring unit
12 storage unit
13 control routine
14.1 coarse tuning routine
14.2 fine tuning routine
ss control signal
WI exchange information
RI resonance information
RF resonant frequency or coarse tuned resonant frequency
RF* fine tuned resonant frequency
ΔF tuning frequency
F frequency

What is claimed is:

1. A method for controlling an ultrasonic unit of an ultrasonic cleaning system comprising at least one control unit, one generator unit and one hand-held unit containing the ultrasonic unit and one switching module provided for starting the ultrasonic unit, wherein mechanical oscillations can be generated via the ultrasonic unit and transmitted to an instrument that is mechanically connected to the ultrasonic unit, wherein after actuating the switching module by a control routine executed in the control unit, a resonant frequency required for operation of the ultrasonic unit in resonance is determined and a control signal (ss) based on the determined resonant frequency is generated in the generator unit and is sent to the ultrasonic unit for operation of the ultrasonic unit in resonance wherein a coarse tuned resonant frequency of the ultrasonic unit is determined by means of a coarse tuning routine executed in the control unit.

2. The method according to claim 1, wherein for coarse tuning of the resonant frequency, a frequency (F) of the control signal (ss) is decreased incrementally from a highest frequency of a first or second frequency range (FB1, FB2) to a lowest frequency of the first or second frequency range (FB1, FB2), and after each decrease the corresponding current amplitude of the control signal (ss) is determined for a respective configured frequency (F) and the frequency (F) at which the maximum current amplitude is measured is selected as the coarse tuned resonant frequency.

3. The method according to claim 1, wherein based on the coarse tuned resonant frequency, a fine tuned resonant frequency is determined by means of a fine tuning routing executed in the control unit.

4. The method according to claim 3, wherein in the event of a deviation of the fine tuned resonant frequency (RF*) from the coarse tuned resonant frequency (RF), the latter is replaced by the fine tuned resonant frequency (RF*).

5. The method according to claim 3, wherein the coarse tuned resonant frequency or fine tuned resonant frequency is stored in a storage unit provided in the ultrasonic cleaning system.

6. The method according to claim 5, wherein after changing the hand-held unit containing the ultrasonic unit and/or the instrument, at least one exchange information (WI) is generated by the control routine executed in the control unit.

7. The method according to claim 6, wherein after actuation of the switching module by the control routine executed in the control unit, the existence of exchange information (WI) is checked, that if exchange information (WI) exists, the coarse tuned resonant frequency is determined anew and if no exchange information (WI) exists, an allocated coarse tuned resonant frequency is loaded from the storage unit.

8. The method according to claim 1, wherein at least one pre-defined first frequency range (FB1) is analyzed in order to determine the coarse tuned resonant frequency.

9. The method according to claim 7, wherein based on the value of the exchange information (WI) or a resonance information (RI), a first or second pre-defined frequency range (FB1, FB2) is analyzed in order to determine the coarse tuned resonant frequency.

10. The method according to claim 9, wherein for analysis of the first or second pre-defined frequency range (FB1, FB2), it is analyzed incrementally.

11. The method according to claim 7, wherein the limits of a first or second pre-defined frequency range (FB1, FB2) can be specified for individual users.

12. The method according to claim 1, wherein for coarse tuning of a resonant frequency, a frequency (F) of the control signal (ss) is increased incrementally from a lowest frequency of a first or second frequency range (FB1, FB2) to a highest frequency of the first or second frequency range (FB1, FB2), and after each increase the corresponding current amplitude of the control signal (ss) is determined for a respective configured frequency (F) and the frequency (F) at which the maximum current amplitude is measured is selected as the coarse tuned resonant frequency.

13. The method according to claim 3, wherein for fine tuning, a frequency (F) of the control signal (ss), based on the coarse tuned resonant frequency is increased incrementally by a pre-defined tuning frequency (ΔF), and after each increase the current amplitude of the control signal (ss) having a resulting frequency (RF+ΔF) is determined and that in the event of an increasing current amplitude the resulting frequency (F+ΔF) is again increased by the pre-defined tuning frequency (ΔF), and in the event of a decreasing current amplitude the previous frequency (RF+(n−1)*ΔF) is selected as the fine tuned resonant frequency (RF*).

14. The method according to claim 3, wherein for fine tuning, the frequency (F) of the control signal (ss), based on the coarse tuned resonant frequency is decreased incrementally by a pre-defined tuning frequency (ΔF), and after each decrease the current amplitude of the control signal (ss) having the resulting frequency (RF−ΔF) is determined and that in the event of an increasing current amplitude the resulting frequency (F−ΔF) is again decreased by the pre-defined tuning frequency (ΔF), and in the event of a decreasing current amplitude the previous frequency (RF−(n−1)*ΔF) is selected as the fine tuned resonant frequency.

15. An ultrasonic cleaning system with an ultrasonic unit provided in a hand-held unit, said ultrasonic unit being connected by means of first connecting lines with a control device, the control device comprising a control unit, a generator unit, a measuring unit and a storage unit and being controllable by means of a switching module connected by means of second connecting lines with the control device, and in which at least one instrument, which can be set in oscillation mechanically by means of the ultrasonic unit, is connected to the ultrasonic unit, wherein at least one control routine is provided in the control unit for controlling the ultrasonic unit, by means of which the resonant frequency needed for operation of the ultrasonic unit in resonance is determined, that the generator unit for generating a control signal (ss) based on the determined resonant frequency is provided, the control signal is sent to the ultrasonic unit for operation of the ultrasonic unit in resonance wherein a coarse tuned resonant frequency of the ultrasonic unit is determined by means of a coarse tuning routine executed in the control unit.

* * * * *